(12) United States Patent
Oster (10) Patent No.: US 11,514,327 B2
(45) Date of Patent: Nov. 29, 2022

(54) APPARATUS AND METHOD FOR UTILIZING A PARAMETER GENOME CHARACTERIZING NEURAL NETWORK CONNECTIONS AS A BUILDING BLOCK TO CONSTRUCT A NEURAL NETWORK WITH FEEDFORWARD AND FEEDBACK PATHS

(71) Applicant: Orbai Technologies, Inc., Gilroy, CA (US)

(72) Inventor: Brent Leonard Oster, Gilroy, CA (US)

(73) Assignee: ORBAI TECHNOLOGIES, INC., Gilroy, CA (US)

( * ) Notice: Subject to any disclaimer, the term of this patent is extended or adjusted under 35 U.S.C. 154(b) by 779 days.

(21) Appl. No.: 16/437,838

(22) Filed: Jun. 11, 2019

(65) Prior Publication Data

US 2019/0385704 A1    Dec. 19, 2019

Related U.S. Application Data

(60) Provisional application No. 62/687,179, filed on Jun. 19, 2018, provisional application No. 62/809,297, filed on Feb. 22, 2019.

(51) Int. Cl.
  *G06N 3/08*   (2006.01)
  *G06N 3/10*   (2006.01)
  (Continued)

(52) U.S. Cl.
  CPC ............. *G06N 3/086* (2013.01); *G06N 3/049* (2013.01); *G06N 3/0445* (2013.01);
  (Continued)

(58) Field of Classification Search
  CPC ......... G06N 3/082; G06N 3/086; G06N 3/105
  See application file for complete search history.

(56) References Cited

U.S. PATENT DOCUMENTS

2004/0143559 A1 * 7/2004 Ayala .................... G06N 3/086
                                                        706/26
2008/0065575 A1 * 3/2008 Szathmary ............. G06N 3/086
                                                        706/27

(Continued)

FOREIGN PATENT DOCUMENTS

CN        112352248 A      2/2021
WO        2019246116 A1   12/2019

OTHER PUBLICATIONS

Samajdar, Ananda, et al. "Genesys: Enabling continuous learning through neural network evolution in hardware." 2018 51st Annual IEEE/ACM International Symposium on Microarchitecture (Micro). IEEE, 2018. (Year: 2018).*

(Continued)

*Primary Examiner* — Hal Schnee
(74) *Attorney, Agent, or Firm* — Franklin & Associates International Inc; Matthew Lambrinos (57) ABSTRACT

A method of forming a neural network includes specifying layers of neural network neurons. A parameter genome is defined with numerical parameters characterizing connections between neural network neurons in the layers of neural network neurons, where the connections are defined from a neuron in a current layer to neurons in a set of adjacent layers, and where the parameter genome has a unique representation characterized by kilobytes of numerical parameters. Parameter genomes are combined into a connectome characterizing all connections between all neural network neurons in the connectome, where the connectome has in excess of millions of neural network neurons and billions of connections between the neural network neurons.

17 Claims, 9 Drawing Sheets

(51) Int. Cl.
   *G06N 3/12* (2006.01)
   *G06N 3/04* (2006.01)
(52) U.S. Cl.
   CPC ........... *G06N 3/0454* (2013.01); *G06N 3/105* (2013.01); *G06N 3/126* (2013.01)

(56) References Cited

U.S. PATENT DOCUMENTS

| | | | |
|---|---|---|---|
| 2013/0073500 A1* | 3/2013 | Szatmary | G06N 3/105 706/15 |
| 2014/0344013 A1* | 11/2014 | Karty | G06N 3/126 705/7.29 |
| 2016/0078361 A1 | 3/2016 | Brueckner et al. | |
| 2019/0026431 A1* | 1/2019 | Grouchy | G16B 40/00 |
| 2022/0215267 A1 | 7/2022 | Oster | |

OTHER PUBLICATIONS

International Search Report dated Aug. 22, 2019, for PCT Application No. PCT/US2019/037758, filed on Jun. 18, 2019, 2 pages.
Van den Heuvel, M.P. et al. (2013). "Network hubs in the human brain," Trends Cogn. Sci. 17:683-696.
Written Opinion of the International Searching Authority dated Aug. 22, 2019, for PCT Application No. PCT/US2019/037758, filed on Jun. 13, 2019, 3 pages.
Zhou, X. et al. (2002). "Construction of genomic networks using mutual-information clustering and reversible-jump MCMC predictor design," 4 total pages.

* cited by examiner

APPARATUS AND METHOD FOR UTILIZING A PARAMETER GENOME CHARACTERIZING NEURAL NETWORK CONNECTIONS AS A BUILDING BLOCK TO CONSTRUCT A NEURAL NETWORK WITH FEEDFORWARD AND FEEDBACK PATHS

CROSS-REFERENCE TO RELATED APPLICATION

This application claims priority to U.S. Provisional Patent Application Ser. No. 62/687,179, filed Jun. 19, 2018 and U.S. Provisional Patent Application Ser. No. 62/809,297, filed Feb. 22, 2019, the contents of each specified patent application are incorporated herein by reference.

FIELD OF THE INVENTION

This invention relates generally to artificial neural networks. More particularly, this invention is directed toward a process and tools using a parameter genome characterizing neural network connections as a building block to construct a neural network with feedforward and feedback paths.

BACKGROUND OF THE INVENTION

Existing multilayer, densely connected, deep neural networks are not a close analogy to true biological neural networks. They are simply large mathematical functions with an enormous number of parameters (static connection weights), fitted to larger amounts of data via backpropagation and a variant of iterative adjustment like gradient descent. Even recurrent neural networks that work with time-series data still just fit data to functions. Existing deep neural networks are very limited in the depth and breadth of problems they can solve compared to biological brains.

Real brains get much of their computing, sensory processing and body-controlling capability from the fact that signals travel through the brain, in complex, time-dependent circuits that can process spatial and temporal data, store information in short-term memory, do operations in it, and even have feedback loops to make circuits like timers or oscillators, or neurological circuits that activate in a repeatable, cascading pattern to send specific time-dependent patterns of controlling signals, for example, to controlling groups of muscles. These networks also learn by directly strengthening connections between neurons that repeatedly fire. They are also organized such that this produces useful learning and training in the neural network. It would be desirable to capture some of this complexity in artificial neurons (and networks of them), while not having to completely model all the electrochemical processes in a real biological neuron, but still producing some of the novel, time-dependent signal processing capability that gives biological brains more utility than what we have today in deep learning neural networks.

Spiking neural networks are artificial neural networks with more brain-like operation with spatial-temporal signals or spikes that move along connections and are integrated at neurons and synapses, making them able to do more advanced computing than traditional deep learning neural networks. They are challenging to work with and train to do specific tasks. Therefore, there is a need for tools, methods, and processes for designing, training and evolving spiking neural networks, of which a subset can also work for deep learning networks.

SUMMARY OF THE INVENTION

A method of forming a neural network includes specifying layers of neural network neurons. A parameter genome is defined with numerical parameters characterizing connections between neural network neurons in the layers of neural network neurons, where the connections are defined from a neuron in a current layer to neurons in a set of adjacent layers, and where the parameter genome has a unique representation characterized by kilobytes of numerical parameters. Parameter genomes are combined into a connectome characterizing all connections between all neural network neurons in the connectome, where the connectome has in excess of millions of neural network neurons and billions of connections between the neural network neurons.

BRIEF DESCRIPTION OF THE FIGURES

The invention is more fully appreciated in connection with the following detailed description taken in conjunction with the accompanying drawings, in which.

Like reference numerals refer to corresponding parts throughout the several views of the drawings.

DETAILED DESCRIPTION OF THE INVENTION

This invention is in the field of artificial neural networks, which are comprised of artificial neurons simulated in software or hardware that integrate input signals and send signals to other neurons via simulated connections. There can be thousands of connections going from each neuron to other surrounding neurons, with synapses along each connection that modify the signals between the neurons and the synapses are in turn modified by the passage of the signals, learning. The description of all the geometry of these neurons, and connectivity of the connections and properties of the synapses is called a connectome, which completely characterizes the neural network. Disclosed are novel methods for characterizing the connectome with a compact parameter genome, and training spiking neural networks with a novel feedback architecture, using both to do efficient genetic algorithms to evolve spiking neural networks to specific purposes. Genetic algorithms rely upon biologically inspired operators, such as mutation, crossover and selection.

Disclosed is a process for designing, connecting, training, and evolving neural networks to a specific functionality. To accomplish this, we construct an artificial neural network as a set of layers and define a set of numbers, called a parameter genome that can completely characterize all of the connections between all of the neurons in these layers. The process takes small sets of the parameters from the genome, inputs them into procedural algorithms to generate two-dimensional (2D) probability maps defining how connections to a layer are distributed in the plane of that layer. In addition, a weight is assigned for how many connections go to each layer above and below a given neuron layer, rendering a 3D distribution of connections when combined with a 2D probability map for each layer. When given a random seed, combined with stochastic sampling of this 3D probability distribution, this allows one to algorithmically compute to which target neuron the connections from the source neuron map to, and to expand these distributions deterministically into a much larger connectome for the entire neural network via this process. Genetic algorithms are used to search the small space of the parameter genomes that expand into the full neural network connectomes, which are trained, evaluated, and selected for which of their genomes to crossbreed for the next iteration, allowing simulated evolution of large artificial neural networks, up to billions of neurons and trillions of connections (and beyond) to focus them to best perform certain tasks. For training spiking neural networks, we make use of a feedback loop consisting of two complementary spiking neural networks with opposite functions and signal directions that send signals to one another in a manner that allows them to train for tasks. The optimal feedback learning connectome that meets the training and performance metrics are evolved as a result of this entire process.

Figure 1:
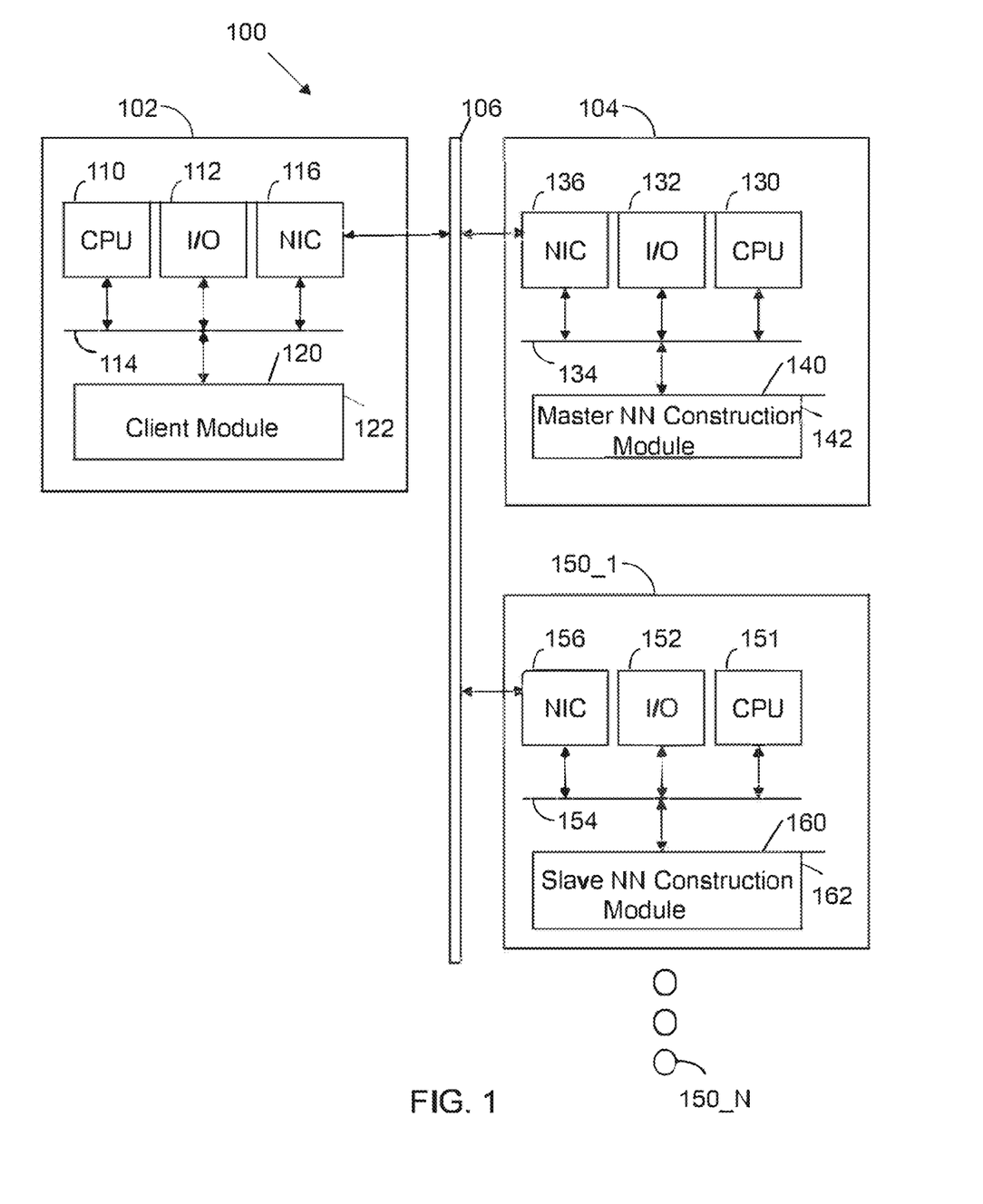
FIG. 1 illustrates a system configured in accordance with an embodiment of the invention.

FIG. 1 illustrates a system 100 configured in accordance with an embodiment of the invention. The system 100 includes a client machine 102 connected to a server 104 via a network 106, which may be any combination of wired and wireless networks. The client machine 102 includes a processor (i.e., central processing unit) 110 and input/output devices 112 connected via a bus 114. The input/output devices may include a keyboard, mouse, touchpad and the like. A network interface circuit 116 is also connected to the bus 114 to provide connectivity to network 106. A memory 120 is also connected to bus 114. The memory 120 stores instructions executed by processor 110 to implement client or end user operations disclosed herein. For example, the memory 120 may store a client module 122, which communicates with server 104 to receive graphical user interfaces to coordinate operations disclosed herein. Examples of such graphical user interfaces are provided below. The graphical user interfaces facilitate the construction of the neural network disclosed herein.

Server 104 includes a processor 132, input/output devices 132, a bus 134 and a network interface circuit 136. A memory 140 is connected to bus 134. The memory 140 stores a master neural network construction module 142 with instructions executed by processor 130 to implement operations disclosed herein. The master neural network construction module 142 coordinates operations performed by a set of slave neural network construction machines 150_1 through 150_N.

Each slave neural network construction machine 150 includes a processor 151, input/output devices 152, a bus 154 and a network interface circuit 156. A memory 160 is connected to bus 154. The memory 160 stores a slave neural network construction module 162 with instructions executed by processor 151.

System 100 is an example of a system that may be used to disclose the operations disclosed herein. Many alternate network configurations may also be used. It is the operations of the invention that are significant, not the particular computer architecture used to implement the operations.

The master neural network module 142 and slave neural network modules 162 constitute a software tool that provides graphical user interfaces to client machine 102 for designing neural networks, such as spiking neural networks. Disclosed are techniques to allow a user to lay out the layers of neural network neurons, connect them up algorithmically with parametric procedural maps system, crossbreed and mutate them to generate a population of similar neural networks, then run simulations on them, train them, cull the underperformers, and then crossbreed the top performing designs and continue the genetic algorithms until a design emerges that meets the performance criteria set by the designer.

Figure 2:
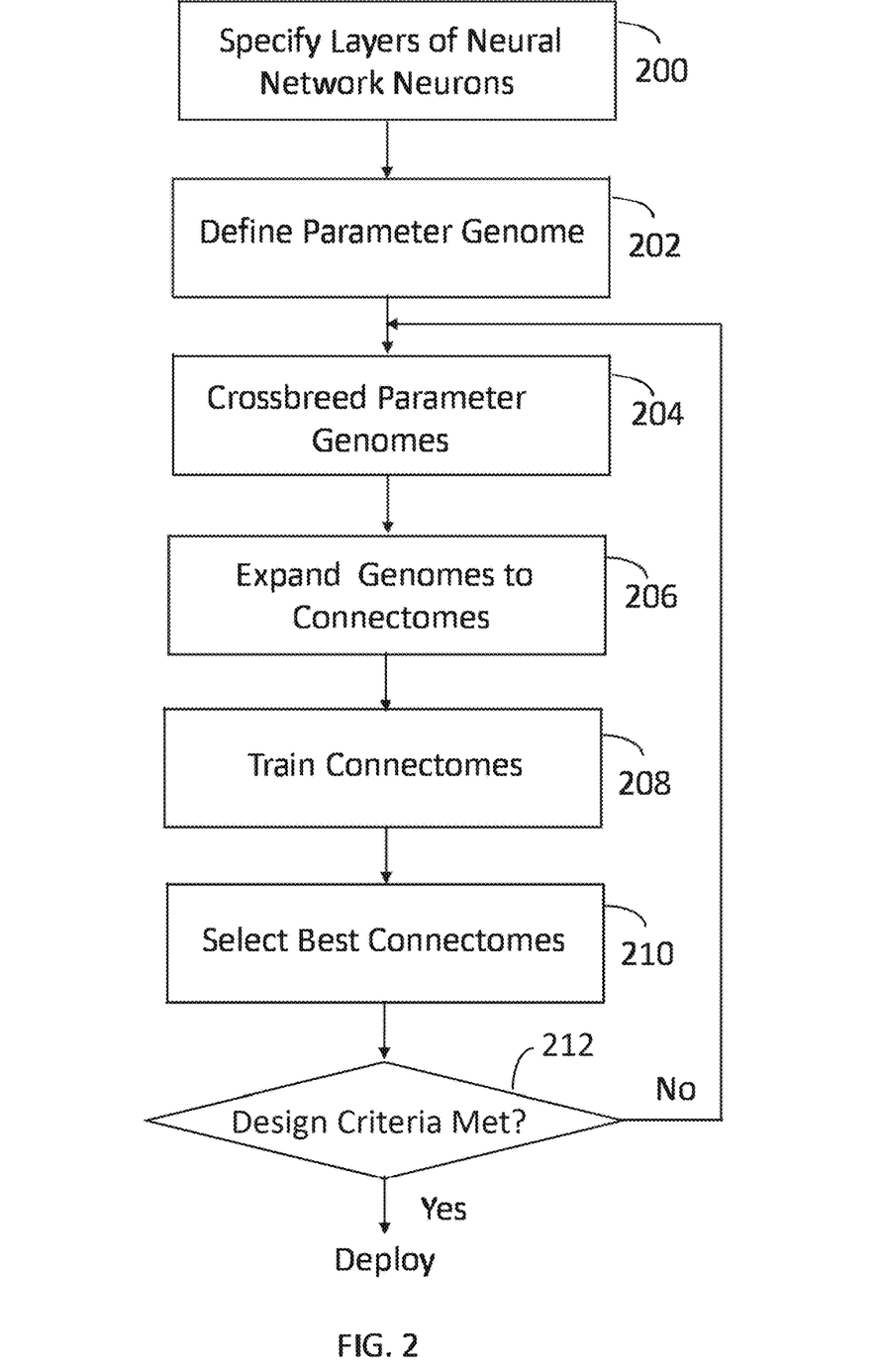
FIG. 2 illustrates processing operations performed in accordance with an embodiment of the invention.
Figure 3:
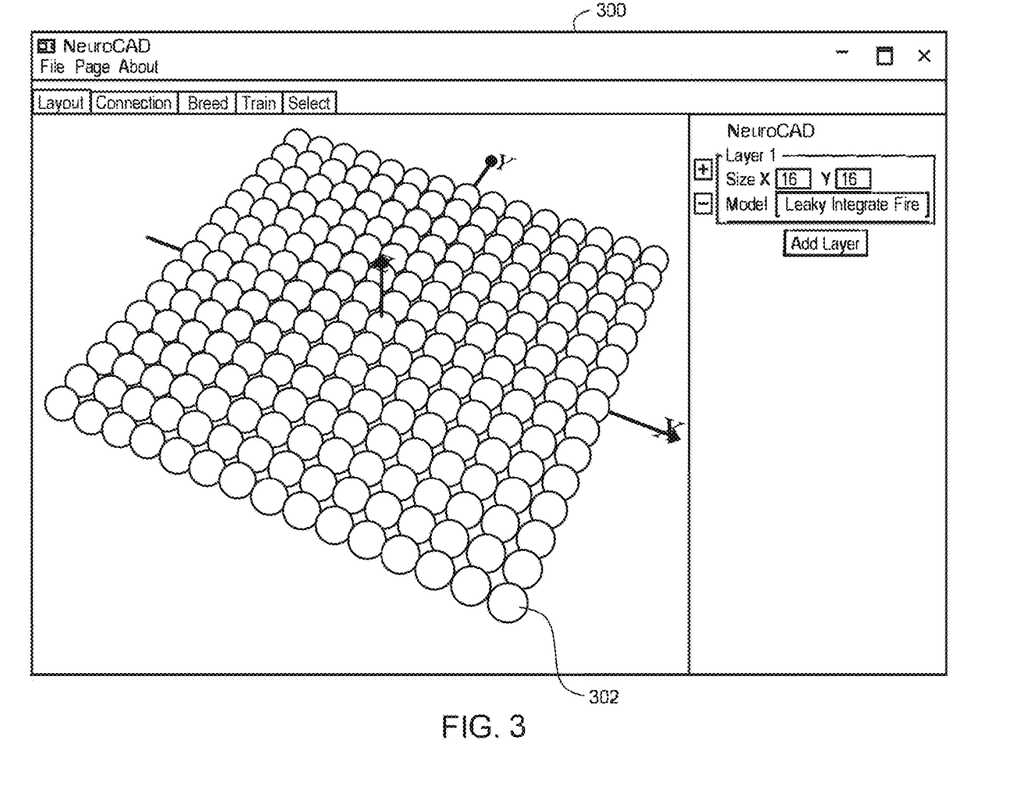
FIG. 3 is a graphical user interface to display a layer of neurons that may be configured in accordance with an embodiment of the invention.
Figure 4:
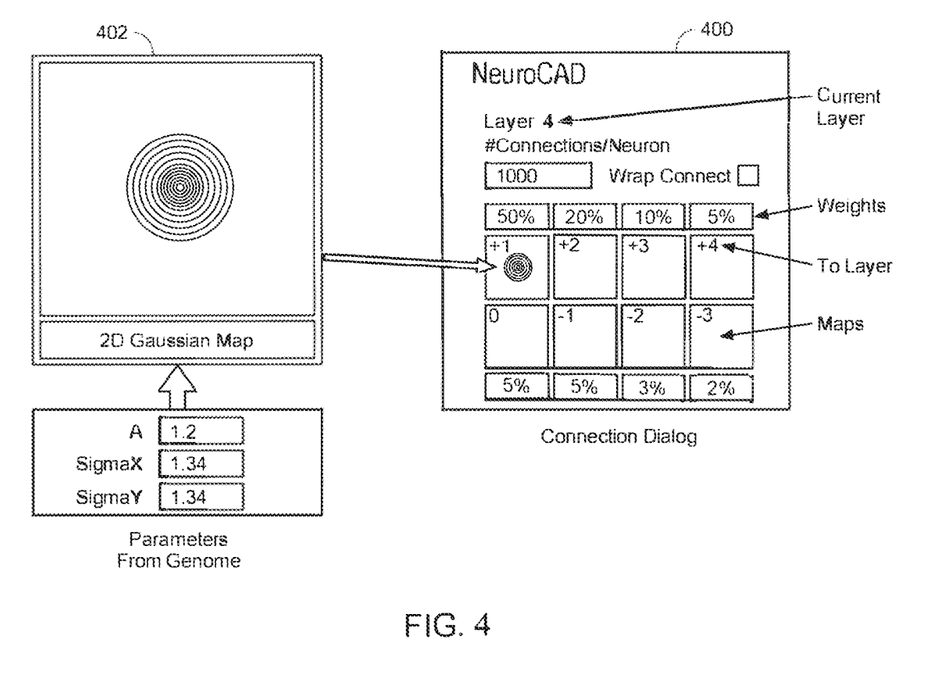
FIG. 4 illustrates a graphical user interface to generate probability maps for neuron connections to other layers by specifying parameters input to a mathematical algorithm to generate a two-dimensional map.

This process is characterized in FIG. 2. Initially, layers of neural network neurons are specified 200. For example, a user authors 'N' neural networks manually in a graphical user interface such as shown in FIGS. 3 and 4. These graphical user interfaces may be provided to the client machine 102 by the master neural network module 142 on server 104. In one embodiment the follow steps are performed:
    a. Layout layers of neurons
    b. Connect the layers
    c. Train the neural net
    d. Evaluate the network performance
    e. Select—Repeat until N networks created
    f. Breed their genomes into N×N new genomes
  2) do distributed training and evaluation in slave machines 150_1 through 150_N
    a. Distribute instances for N×N genomes to servers
    b. Connect those genomes into Connectomes
    c. Train each network on a server instance
    d. Evaluate each network instance
    e. Select the top N networks
    f. Breed their genomes into N×N new genomes
    g. Repeat steps a-f until a network scores high enough in Evaluate.

In one embodiment, first N networks are specified by inputs to a graphical user interface. Alternately, parameters may be loaded from a file. The first N networks are crossbred into N×N networks. Genetic algorithms may be used to evolve them over several generations, while selecting only the networks that perform best against selection criteria to continue with and crossbreed each generation. These operations are specified in the remaining operations of FIG. 2.

FIG. 3 illustrates a graphical user interface 300 with a layer of neurons 302. The user sets the number of layers of neurons, and for each layer, laid out in a grid, the number of neurons in X and Y are specified, the particular neuron simulation model to use for that layer is specified, and other parameters for the layer are specified. This may be done by a user or programmatically. These parameters are filled out per layer. In one embodiment, the neurons in the layers are spaced further apart when there are fewer neurons, making them sparser, so the layer extents are always the same in order to keep the geometry of the connections between them manageable.

Returning to FIG. 2, the next operation is to define a parameter genome 202. This is done by expressing parameters that characterize connections between neurons on different layers. The graphical user interface of FIG. 4 may be used to facilitate this operation.

FIG. 4 illustrates a connection dialog interface 400, which allow one to specify how the neurons in the current layer connect to the neurons in other target layers. The user inputs the number of connections that will extend from each neuron in the current layer, and a percentage weight per target layer that determines how many of those connections go to each of the target layers. In this example, the connections can range from a target layer −3 below the current layer to +4 above the current layer, allowing novel feed forward and feedback behaviors in the network.

In one embodiment, each target layer also has a two-dimensional (2D) grayscale map assigned to it that is generated algorithmically from parameters, using functions like Gaussian or noise generation or combinations thereof. FIG. 4 illustrates a two-dimensional Gaussian map 402 that may be associated with a connection. Each connection may have an associated weight.

In this case, the mathematical function to generate the 2D map is a 2D Gaussian function (400), and the input parameters are:

A—amplitude of the Gaussian (in brightness or Z)
SigmaX—Width in X of the Gaussian
SigmaY—Width in Y of the Gaussian These parameters are a sub-set of the parameter genome, and for each map, for each layer-to-layer connection, there is an additional set of parameters, which, when all combined with the numerical parameters for the layer layouts, and the overall simulation parameters and hyperparameters, uniquely define the parameter genome for a neural network.

Figure 5:
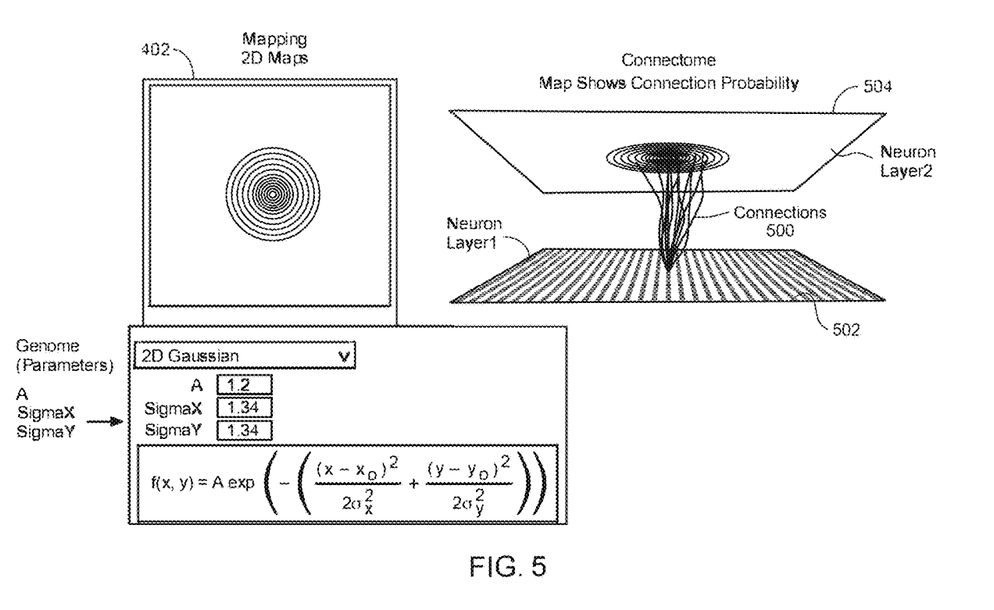
FIG. 5 illustrates using the methods and interfaces in FIG. 4 to establish connections between a neuron in one layer and other neurons on adjacent layers of neurons by reference to the probability maps generated in FIG. 4.

FIG. 5 illustrates a graphical user interface that characterizes specified connections 500 between a first layer 502 and a second layer 504 after parameters are set in the user interfaces 400 and 402. In this example, a two-dimensional Gaussian distribution is used on the target layer 502, so it is most likely to connect to the neurons directly above it on layer 504, and less likely to connect further away, as shown in FIG. 5.

Thus, a small set of numerical parameters, which is referred to as a parameter genome, are used to algorithmically generate a set of procedural two-dimensional grayscale maps which in turn describe the two-dimensional probability distribution of how the neurons of one layer connect with neurons in another layer, and together with weights per target layer, define a three-dimensional probability distribution for connections between layers of neurons. The parameter genome is a compact, fundamental building block that when expanded through a set of mathematical operations, uniquely and deterministically defines the connectome (description of all the connections) of the final neural network.

Running these connected networks with randomly initialized synapse weights in a simulation allows them to learn and progress, then after a set time, their behavior is measured against a performance metric. Only the top networks with the best performance against the metric are retained. Genetic algorithms are subsequently used to crossbreed the source genomes of the successful networks by combining their characteristics randomly and adding mutations, creating new genomes that can then be expanded into networks, trained, and evaluated, and only the top networks are selected for further crossbreeding.

In one implementation, in each cross-breed operation, we give a random chance of growing them slightly in the process by adding more layers and more neurons, and also test them against progressively more difficult and complex performance metrics in an iterative process with the goal of evolving much more advanced networks with greater capability, limited only by computing capability and the quality of the performance metrics.

The parameter genome is a compact representation of the larger structure of the connectome of the full neural network. The compact genome data structure can be crossbred and mutated to use in genetic algorithms much more easily because it has several orders of magnitude fewer parameters than the connectome. Thus, the next operation shown in FIG. 2 is to crossbreed parameter genomes 204. This operation accelerates evolution because small genome changes have larger and more measurable changes in network structure.

An optimization could be biasing the mutation at each stage to prefer changes to newer neural structures allows the evolution to converge more rapidly, by not revisiting past optimizations. This is similar to how the human brain developed, with a genome of about 8000 genes determining brain structure of 100 billion neurons, and with the deeper, more primitive structures maturing earlier in animal brain evolution and remaining relatively fixed thereafter, and the newer structures forming and maturing more recently.

In this process, each gene or parameter genome represents a neural structure composed of many neurons and their connections. We can also create composite macro-structures of neural nets by combining multiple genomes together and using a macro-gene to define their spatial and topological connections and where their inputs and outputs connect. Then when evolving these macro networks, each individual network's gene can still be crossbred and shaped by the evolutionary process as well as the macro-genes being crossbred, which define the macro structure and topology of the macro-network made up of these building blocks. The evolutionary process would alternate between shuffling and mutating the combination of macro-genes (and thus the macro-structures), and then cross breeding and mutating specific genomes representing the sub-networks' structure, which affects the whole larger macro structure in a different modality. Specific genes could evolve that define very specialized neuromorphic sub-processors. Also, once a large network is constructed out of subunits defined by genes, any modification to that gene can affect every instance of the subunit, modifying the macroscopic properties of the entire network with small tweaks.

If we had networks for inputs, and outputs, we could start these out small, and evolve them to perform on simple tasks, like evolving to learn vision on simple flashcards for babies for example. Then a cognitive or integrative network with these networks as inputs could be trained and evolved using cognitive IQ tests for babies, children, teens . . . and gain cognitive functionality with these simple inputs before scaling the input systems like vision, to work with more complex, real world input. By advancing the training, growth and evolution of different sub-networks at different times, and training the whole network with some inputs and outputs simplified, we can accelerate the overall progress of developing advanced macro-networks, or artificial brains, like this.

One can also splice extra genes into the macro-genes from each parent in during the crossbreeding process, making the child network a much larger hybrid of two parents. If this structure gives the new network an advantage, it will continue to propagate, and such rapid growth speeds up the training process.

Returning to FIG. 2, parameter genomes are expanded into connectomes 206. More particularly, the parameter genomes are put through a set of mathematical stages to form a connectome. A connectome characterizes all connections between all neurons in the connectome of the neural network. The neural network connectomes can have on the order of thousands of connections per neuron and contain billions of neurons or more. The parameter genomes are expanded into a connectome in accordance with an algorithmic process with a deterministic mathematical model. In one embodiment, the deterministic mathematical process receives numeric parameter to generate a two-dimensional grayscale map. Multiple two-dimensional grayscale maps may then be combined to produce a final grayscale map.

This combination of the grayscale maps is a mathematical operation to transform the input pixels of the two maps into output pixels of the destination map. An example is a multiply, which is a pixel-by-pixel multiplication of the two input pixels to get the output pixel, which is done for every pixel in the maps. Generation of procedural maps and combining them in mathematical operations is commonly used in many 2D and 3D drawing and modelling software programs for digital art and visual effects, but we show a novel use of them to expand parameters to maps, and compositing those maps using these operations to make a probability map to define connections from neurons in one layer to neurons in another layer.

Connectomes are then trained 208, as referenced above. The best aggregated neural network connectomes are then selected 210 and tested against design criteria 212. If the design criteria is not met (212—No), control returns to blocks 204-212. If the design criteria is met (212—Yes), the final neural network is deployed.

Returning to FIG. 5, it can be appreciated that the disclosed technique allows one to combine several maps with blend operations to create a unique map, which is then applied to the target layer, centered above the source neuron, and is used as a probability distribution to compute which neurons in the target layer receive connections from the source neuron.

This allows one to carefully shape the connection pattern for different applications, like small circular spots directly above the current neuron, as shown in FIG. 5. Thus, different patterns may be used for different functions, such as vision, sound, speech, cognition, or motor control, just like a human brain has unique neural geometries for each function. This also allows one neural architecture and description of that architecture to be specialized to many tasks and functions by this flexible connectome scheme.

A connectome is a complete description of all the connections between all neurons in a neural net. This disclosed parameter genome allows one to completely specify the neural connection configuration of a very large connectome (billions of neurons with thousands of connections each) with just a relatively small number (e.g., a few kilobytes) of numerical parameters that uniquely represent it. Starting with the same random seed, each small parameter genome will deterministically reproduce the exact same large connectome every time. Smooth variations of the parameters and interpolations between them also result in smooth variations in the 2D maps, and in the resultant connectomes, which also interpolate. This is invaluable for genetic algorithms that converge quickly.

Figure 6:
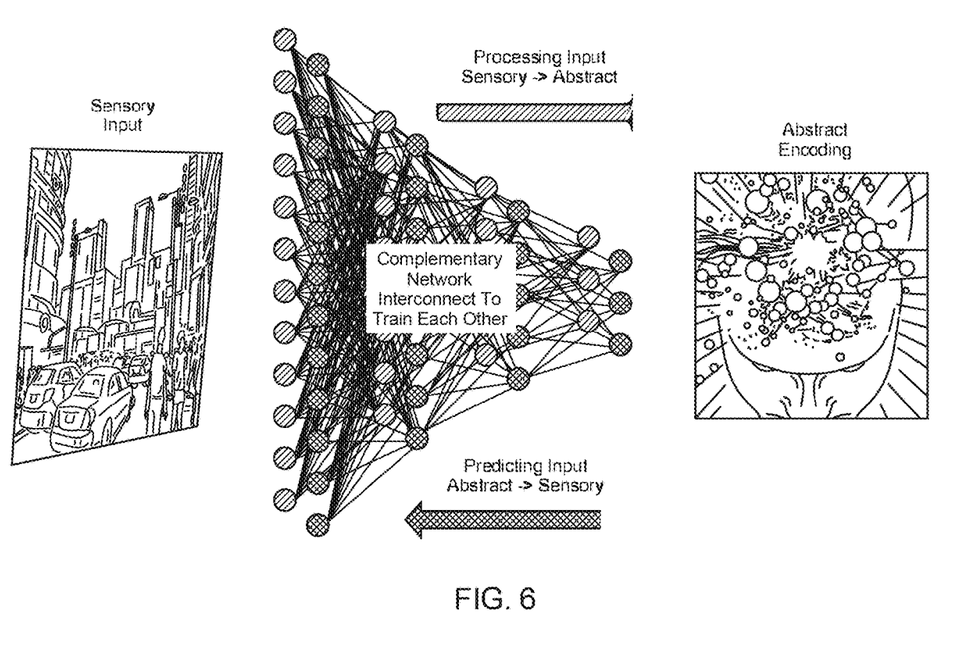
FIG. 6 illustrates complementary networks interconnected to train each other in accordance with an embodiment of the invention.

To train connectomes 208, one may use a bidirectional feedback loop in a spiking neural net architecture. This feedback loop has two separate networks with complementary functions. For instance, if one network takes in images or video and compresses it to a compact, machine-readable representation, then the other network decompresses this compact representation back to match the full input data. This process is depicted in FIG. 6.

By interconnecting and feeding back into each other in the right way, these networks train each other to do their complementary functions. For instance, layer N of the compression network would feed back into layer 0, alongside the output, and layer N of the decompression network would feed back into the layer 0, adding to the input, and amplifying it the more they match, giving a positive feedback that converges the networks to train and do their functions.

Figure 7:
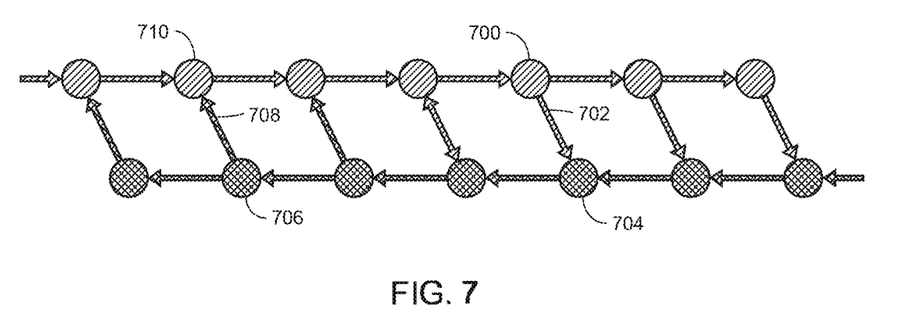
FIG. 7 illustrates connections between two networks so that the two networks can exchange information and interact with each other in a feedback loop in accordance with an embodiment of the invention.

FIG. 7 illustrates neuron 700 from a first layer passing information via path 702 to a neuron 704 of a second layer. Similarly, neuron 706 of the second layer passes information via path 708 to neuron 710 of the first layer.

Figure 9:
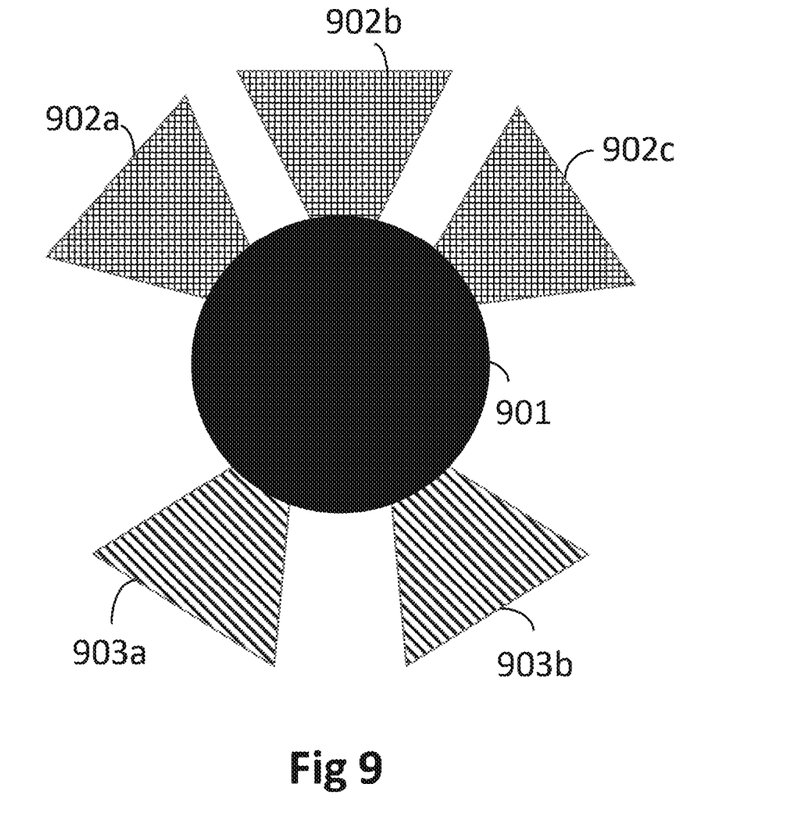
FIG. 9 illustrates several neural networks meeting in a central network, some feeding input into the central network, others carrying output from it.

FIG. 9 illustrates feedback neural networks 902a, 902b and 902c being fed into a central neural network 901. For example, the neural networks shown in FIG. 6 and FIG. 7 are used to process different modalities of input (e.g., video, sound, sensors, . . . ). The central neural network 901 does processing, planning, decision making, and other operations based on that input, using either a specialized spiking neural network, or a deep learning network, reinforcement learning, or other conventional decision-making process. The central neural network 901 then produces abstracted outputs to other feedback neural networks 903a, 903b that then expand them into outputs such as motor controls for a robot, or display controls for a readout, or any other output state. This is one implementation of the macro-networks made from a macro-gene, which combines different individual networks made from their genes and defines how they connect spatially and topologically, in this case to connect input and output networks to a central processing network.

At the end of a training cycle, the neural network is evaluated with test inputs and the output from the network is compared to the expected output. The network is given a numerical score based on how well it reproduced the expected output, like a correlation value per input frame that is averaged or numerically weighted.

Figure 8:
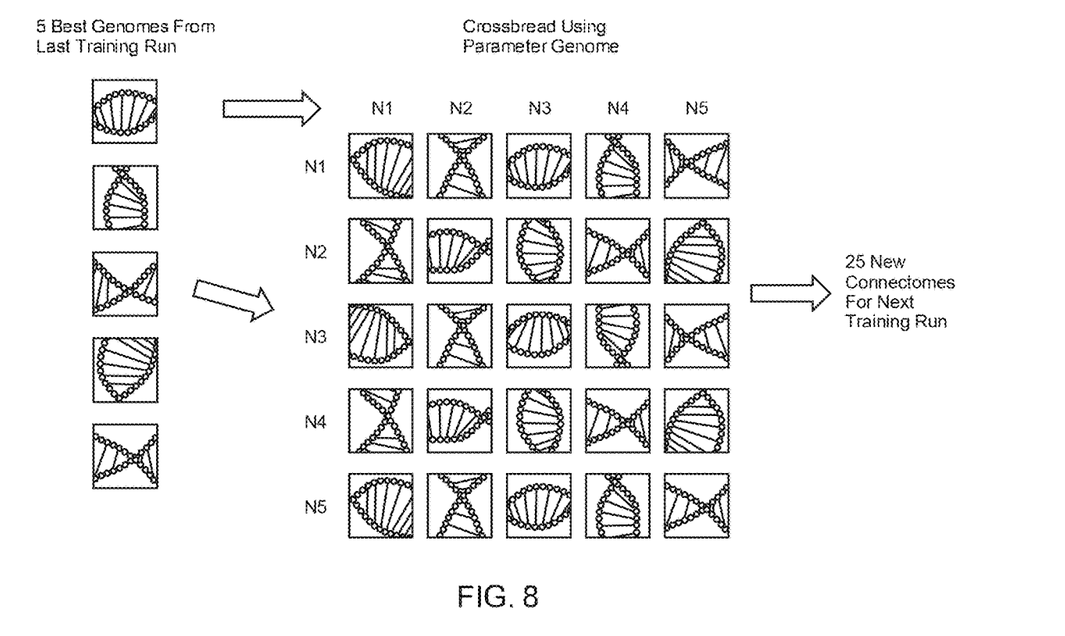
FIG. 8 illustrates parameter genomes crossbred in accordance with an embodiment of the invention.

The top N networks trained and tested are selected to be the basis for genetic algorithms to use in the next generation of networks to be trained. In one embodiment, the parameter genomes from each of the top N networks are crossbred to get N×N new parameter genomes. An embodiment of this is shown in FIG. 8.

In one embodiment, this crossbreeding is done within the genome itself by randomly selecting parameters or sets of parameters from each pair of genomes, such as:

A crossbreed operation can take in two parameter genome structures as input and fill in the members of this parameter genome structure with the results, either by randomly selecting each parameter from one of the parent genomes:

```
if (rand( ) < HALF_RAND_MAX)
{
    A = parameterGenome1.A;
}
else
{
    A = parameterGenome2.A;
}
```

Or crossbreed by interpolating using the two parameters:

$t=\text{rand}(\ )/\text{RAND\_MAX}$ $A=t*\text{parameterGenome1}\cdot A+(1-t)*\text{parameterGenome2}A;$ Or crossbreed by interpolation/extrapolation using the two parameters, where the result can be outside of their interpolation space:

$t=(1+\text{ext})*\text{rand}(\ )/\text{RAND\_MAX}-(0.5*\text{ext})$ $\text{diff}=\text{parameterGenome2}\cdot A-\text{parameterGenome1}\cdot A;$ $A=\text{parameterGenome1}\cdot A+t*\text{diff};$ In addition, a proportional random mutation can also be added to the final value to create more variation:

$m=\text{rand}(\ )/\text{RAND\_MAX}$ $A+=(m-0.5)*\text{mutationScale}*A;$

With a small set of a few hundred parameters, one can have a unique numerical gene that can uniquely generate one connectome amongst millions of possibilities. This facilitates the use of genetic algorithms where one can crossbreed these parameter sets with simple math as above, giving one new genes of parameters that can quickly generate a wide variety of connectome schemes.

The two-dimensional maps change smoothly as the parameters change, and so the connectomes also change smoothly with the parameter genomes changing. Parameter genomes that are close to each other numerically produce connectomes that are close to each other as well, and one can smoothly interpolate between them. These properties are vital for doing genetic algorithms where two genomes are crossbred or mixed to generate a new genome, which then expands to a novel connectome to train and evaluate. Without these properties of the genomes and connectomes varying smoothly together, and interpolating proportionally, genetic algorithms would not converge to useful solutions.

The master neural network module 142 may create N×N genomes by breeding N input network genomes and send them out to machines 150_1 through 150_N as N×N instances (each with a different genome parameter file). Processing on each instance may include:
  a. Load a unique parameter genome from the above crossbreed operation.
  b. Connect network by expanding genome to network connectome.
  c. Train all instances with input data from a common data server.
  d. Evaluate test network vs performance criteria.
  e. Select top 'N' network candidates from all trained simulations based on above score.
  f. Crossbreed their parameter genomes to get N×N new candidate genomes.
  g. Repeat until a network meeting the performance criteria has been evolved.

By evolving generations of neural networks and picking the best each generation (based on specific selection criteria), one can start with very general-purpose neural networks and evolve them to specific functions, like vision, video compression, speech recognition, natural language processing, and control algorithms, by picking specific training datasets and selection criteria to drive them in that direction.

One can also start with simpler neural networks and selection criteria and progressively increase the size and complexity of the neural nets during evolution while making the performance criteria more sophisticated and testing greater complexity and depth of function with each generation. This allows one to evolve very sophisticated networks capable of compound functionality from simpler roots.

One can also keep updating a data server with more new data and keep re-evolving the neural networks as the data is added. This could be done for a distributed fleet of cars, with the data constantly coming in from sensory systems of all cars and being stored centrally. The data is then used to train, evolve, and update the artificial intelligence on a regular interval then send it out to update the whole fleet.

Properly set up, genetic algorithms are a very powerful method for finding solutions to very complicated problems that are intractable to normal mathematical optimization methods. However, setting them up can be tricky. If one built a 1 million neuron network with a billion connections (connectome), and made 100 copies of it, each with slightly different connections modified one by one with an algorithm, then applied genetic algorithms using changes to the connectome as the basis for breeding, it would never work. The space of one billion connections that we are trying to search is too large, and even with infinite compute power one would not converge on a useful neural network.

This is why the compact parameter genome is the basis set that is used for all the breeding operations. When the expansion/unpacking/decompression is applied of each new genome to get a unique connectome, it is a meaningful one. A small gene that will reliably re-create the same connectome is needed. It must also do so in a deterministic fashion, so one can always reproduce it. Slight variations to the genome should produce connectomes that are close to each other as well, otherwise genetic algorithms will not work very well.

In one embodiment, each neuron has at least 1000 connections, and there are millions of neurons in each sheet. One has a probabilistic way to pseudo-randomly connect the neurons, based on a random seed and procedural probability maps that spatially determine where the neurons are likely to connect. This somewhat follows the principle that biological neurons connect by growing and following chemical trails or gradients that have some sort of spatial distribution in the brain. By using composited procedural maps for this, one can start with a set of numerical parameters that are selected to completely describe how the resulting procedural image will look. With these procedural parameters for all the maps, the mixing parameters and per-target-layer weights become the genome for a connectome or connection scheme, one can reproduce it all from a few parameters and a random seed.

Thus, one starts with a parameter genome, applies two-dimensional algorithms and two-dimensional probability maps and a per-layer weight in a set of operations to produce a connectome. A user interface, such as shown in FIG. 5 may be used in this process. Consider the case of a neuron in the center of layer 502, as shown in FIG. 5. It is determined which neurons it will connect to in layer 504. One may use a two-dimensional Gaussian distribution centered right above the neuron on layer 504, so it is most likely to connect to the neurons directly above it, and less likely to connect further away. Alternately, one may use a procedural fractal, which has the neuron able to connect in a wide area on layer 504 but following a specific pattern. There are thousands of publicly available algorithms for two-dimensional mathematical, fractal, and procedural maps, and each of their parameters can be widely varied to produce unlimited variations of maps in the same family.

As shown in FIG. 4, the designer can connect neurons in the present layer to all layers above it and below it, and even itself, controlling the weighting of connections to each layer manually. This gives a lot of control over the feed-forward and feedback behavior of the network. The referenced maps control the distribution of these connections for each layer.

As shown in FIG. 4, for each neuron layer in the Connection screen one has:
1) A list of all other layers it can connect to (−3, . . . 0, . . . +4) in this example
2) For each layer that neurons can connect to one has:
   a. A weight controlling the percentage of connections that go to this layer
   b. A probability map controlling the two-dimensional spatial distribution of connections to neurons in that layer
   c. That map is the result of the Parameter Genome to two-dimensional procedural mapping In general, this is a very flexible and powerful technique to specify the connection scheme, using a small set of parameters to generate procedural or mathematical two-dimensional probability maps, and to composite those to localize and modify them further. With a small set of a few dozen parameters, one can have a unique numerical gene that can uniquely specify one connectome amongst millions of possibilities. This facilitates the use of genetic algorithms where one can crossbreed these parameters mathematically, rendering new genes of parameters that can quickly generate a wide variety of connectome schemes.

Spiking neural networks are a more realistic simulation of how real neurons, neural networks, sensory systems, and intelligence work, with spiking signals that travel between neurons in time, and sophisticated processing and integration of these signals at neurons and synapses. They have distinct advantages over deep learning's simpler feed-forward neural networks.

In a real biological neural network:
The neuronal body integrates inputs from the dendrites coming into it
Integrates incoming signals in both space and time
Some dendrites excite, some inhibit, adding or subtracting from the potential
Neuronal body 'fires' when action potential (−55 mv) is reached across cell wall
When the neuronal body fires, a spike train is transmitted down the axon
Transmitted along axon, branches, and is amplified (and modified) along the way
Signal in time and space that carries more information than a simple amplitude
Spiking signal is further modified at synapse
Axon spike train stimulates neurotransmitter release from pre-synaptic side
Neurotransmitters drift across synapse, modified by ambient neurochemistry
Receptors on a post-synaptic side integrate a chemical signal, firing at a threshold
A spike train propagates down the dendrite to the next neuron
If both the pre- and post-synaptic neuron fire close together the synapse strengthens Feedforward models used in traditional deep neural networks are very simple, with no temporal signals, and just static scalar values only on connections. Deep learning neurons are static with simple summation of scalars followed by a transfer function, or in discrete time-steps like in recurrent neural networks which at best are pseudo-temporal.

Spiking neural networks transmit rich information via spikes trained along dendrites and axons and the signals undergo integration and processing in space and time within the neuronal body, and at the synapses. Because there is latency from one neuron firing until the next, signals travel through a network, with a time-domain behavior, with multiple signals combining to create complex neural circuits that do time-based processing, which can have feedback, loops, or create timed and synchronized chains of impulses for motor control or speech applications. In general, they have much richer and more powerful behavior than deep learning neurons and neural networks.

Although spiking neural networks themselves are prior art dating back to 1955, there has not been a satisfactory solution for training them to date, which has prevented them from being utilized in practical tasks. Conventional deep neural networks can be trained by backpropagation—consisting of feeding information into the network, and comparing the actual output to the (predetermined) expected output, calculating the error between them, and feeding that error backwards through the network in a very specific mathematical operation called backpropagation, and using specific mathematical methods to adjust the weights of the connections in an iterative cycle that takes a lot of computing resources.

However, spiking neural networks cannot be trained by this method because of their time-dependent nature. Spikes are processed irreversibly by neurons, emitted onto connections (axons), then processed irreversibly by a synapse, and then fed into post-synaptic neurons and again processed irreversibly, continuing the cycle. There can be feedback, loops, and other novel circuits, all of this preventing a simple mathematical backpropagation from working with them.

We propose using a novel architecture for training spiking neural network, using two complementary networks to train each other by exchanging information between them as shown in FIG. 6. Specifically, there is one network that transforms input data into output data, usually going from a raw input (or output) format to a more compact, machine-learned representation, encoding it. Then there is a second, complementary network of similar construction except the signals flow in the opposite direction, and it does the opposite transformation, decoding the abstract, machine-learned representation back into the raw input format. This pair of complementary networks forms an auto-encoder trained to encode and decode the input back into the same format and data.

These two networks are interconnected in a manner such that the signals from one influence the neural activity in the other, as depicted in FIG. 7. One proposed configuration is where the output of each network feeds back into the input of the other network, creating a feedback loop between them. In addition, there could be information passed between the intermediate layers as well, to augment this feedback loop.

Because human beings have no intuition or knowledge about how to actually construct these feedback loops optimally, and the design space is very large, we will use the genetic algorithms to explore the best configurations, as we describe elsewhere in this work, feeding in some candidate networks that span a possible solutions space, and then letting it evolve the best network configuration with the feedback mechanism that is most accurate and efficient given our training data and performance criteria.

Returning to FIG. 6, it should be appreciated that the disclosed pair of complimentary networks constituting an auto-encoder may be combined with another pair of complimentary networks comprising another auto-encoder so they are joined at the ends where the machine-learned, compact data is represented. For example, the input processed by the set of complementary networks of FIG. 6 produces abstract encoding, such as encoding the sequence of images in a video to a compressed data format, as in our above auto-encoder example. A second set of complementary networks may autoencode a different modality of data, for example sound with speech, which has been pre-processed into a 2D spectrum waterfall display, which is then encoded into the same machine-learned encoding format at a center layer shared as an interface between the two complementary networks. This allows the result of two different modalities of input to be simultaneously be fed in each end and encoded to the same machine-learned representation and decoded back out from the common abstract representation to the original input, just like our auto-encoder example. A key difference is now that there is a common, compact, encoded abstract representation, we can feed input of one modality in one format (video for example) in one end, have it encode to the common compact representation, and then have the decoder on the other network decode that to the other format on the other end (speech for example). In an example, this network could watch a video of objects, and listen to their spoken names, and learn to autoencode both the video and audio inputs to the same internal format and learn to associate them. Once trained, you could show it a video clip, it will encode it to the common format, decode that to the associated audio, and speak the name associated with this object. This is very powerful, as these bimodal auto-encoders learn the complementary operations of how to reproduce the input of the opposite modality, learning to speak by listening, learning to create video by watching. This has enormous utility in artificial intelligence.

These auto-encoders would typically go from dense layers with many neurons to sparse layers with fewer neurons in order to facilitate the compaction of the data. One advance on this is to put a bimodal auto-encoder as above, but the sparse end of each auto-encoder plugged in to opposite sides of a block of layers in the middle where it becomes dense again, and with a partial feedback loop feeding signals back into that block, from each of its ends. With the internal connections properly configured it becomes a computational engine that can have feedback loops that hold short-term memory, process operations on it, and produce much more useful output from the inputs than just the simple dual auto-encoder above. We can train this to do more advanced cognitive feats and have more advanced performance criteria that it can be evolved to meet.

In fact, this is an example of a seed AI, with input, output, and computation embodied in a neural architecture. By evolving this to become larger, with the addition of more input and output modalities, and a larger cognitive 'core', we can produce progressively more advanced artificial 'brains' like we describe with the macro-gene representation in FIG. 9 and evolution. Again, there are no theoretical limits to how large, complex, and advanced these brains could become, and they are only limited by the computational resources available, and the cleverness of the designer in coming up with staged performance criteria that become progressively more advanced and challenging as the brain grows and evolves, and allow them to evolve and train to a productive end.

An embodiment of the invention utilizes a computer software (or hardware) simulation of a simplified neuron that has signals that take time to travel between neurons (lag), that have synapses between neurons that integrate incoming signals, modify them and delay them before transmitting them across, and neuromorphic bodies that sample and integrate incoming time-domain signals and compute when to emit an 'axonal' time-dependent signal, and how to shape it. These artificial synapses will also modify their integration function every time a signal passes and strengthen or weaken the 'connection' of the synapse based on whether or not both neurons on either side fire together within a certain time interval. This makes a more brain-like neural network that can produce complex, travelling signals, and learn. These integration operations and time-dependent signal behaviors can all be varied to produce artificial neurons with different characteristics, behavior and efficiency. Networks of these neurons would exhibit travelling signals, waves, feedback loops, and much more brain-like complex processing.

An embodiment of the present invention relates to a computer storage product with a computer readable storage medium having computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs, DVDs and holographic devices; magneto-optical media; and hardware devices that are specially configured to store and execute program code, such as application-specific integrated circuits ("ASICs"), programmable logic devices ("PLDs") and ROM and RAM devices. Examples of computer code include machine code, such as produced by a compiler, and files containing higher-level code that are executed by a computer using an interpreter. For example, an embodiment of the invention may be implemented using JAVA®, C++, or other object-oriented programming language and development tools. Another embodiment of the invention may be implemented in hardwired circuitry in place of, or in combination with, machine-executable software instructions.

The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, they thereby enable others skilled in the art to best utilize the invention and various embodiments with various modifications as are suited to the particular use contemplated. It is intended that the following claims and their equivalents define the scope of the invention.

The invention claimed is:
1. A method of forming a neural network, comprising:
specifying layers of neural network neurons,
defining a parameter genome with numerical parameters characterizing connections between neural network neurons in the layers of neural network neurons, wherein the connections are defined from a neuron in a current layer to neurons in a set of adjacent layers, wherein the parameter genome has a unique representation characterized by kilobytes of numerical parameters, combining parameter genomes into a connectome characterizing all connections between all neural network neurons in the connectome, wherein the connectome has in excess of millions of neural network neurons and billions of connections between the neural network neurons, crossbreeding genomes to form aggregated genomes, expanding aggregated genomes to neural network connectomes, training the neural network connectomes with training, collecting selected aggregated neural network connectomes to form a final composite neural network by combining their genomes and expanding the resulting genomes, wherein training the aggregated neural network connectomes includes applying data to end layers of the neural network and adjusting connection weights in an iterative process, a first spiking neural network processing input information to form a compact format, a second spiking neural network processing the compact format to form the input information, wherein there are connections between the first spiking neural network and the second spiking neural network to exchange information, and wherein output of the first spiking neural network is input to the second spiking neural network and output from the second network is input to the first neural network to establish a feedback loop.

2. The method of claim 1 wherein parameters of the parameter genome are received from a graphical user interface.

3. The method of claim 1 wherein parameters of the parameter genome are loaded from a file.

4. The method of claim 1 wherein parameters of the parameter genome are computed mathematically from an algorithm.

5. The method of claim 4 wherein parameters of the parameter genome are computed from a combination of two other complete parameter genomes.

6. The method of claim 5 wherein parameters of the parameter genome are crossbred by randomly picking each parameter from either a first source genome or a second source genome individually until all parameters are filled.

7. The method of claim 5 wherein parameters of the parameter genome are crossbred by interpolating between or extrapolating from parameters of a first source genome and a second source genome until all parameters are filled.

8. The method of claim 5 wherein parameters of the parameter genome include randomness to create variation.

9. The method of claim 1 wherein combining parameter genomes into a connectome includes combining parameter genomes in accordance with a deterministic mathematical process.

10. The method of claim 9 wherein the deterministic mathematical process receives numeric parameters to generate a two-dimensional grayscale map.

11. The method of claim 10 further comprising combining multiple two-dimensional grayscale maps in a mathematical process to produce a final grayscale map.

12. The method of claim 11 wherein the final grayscale map represents a two-dimensional spatial probability that a neuron on a source layer of neural network neurons will connect to neurons on an adjacent, target layer of neural network neurons.

13. The method of claim 1 wherein the first spiking neural network receives first modality input from one end and forms the compact format at a center layer, and the second spiking neural network receives second modality input from another end and forms the compact format at the center layer.

14. The method of claim 1 where multiple neural networks are used to take in different inputs modalities to reduce each modality to a compact abstraction that is fed into a central artificial intelligence processing network, which then processes the compact abstraction of each input and produces compact, abstract outputs, which are then each expanded by a feedback network to produce detailed outputs for external systems.

15. The method of claim 1 wherein each network is evaluated to give it a numerical score to rank aggregated neural network connectomes, wherein the selected aggregated neural network connectomes have the highest N numerical scores.

16. The method of claim 15 where the numerical score is obtained by providing inputs to a neural network connectome, obtaining outputs, and measuring the outputs against expected outputs.

17. The method of claim 1 further comprising confirming that the final composite neural network satisfies specified design criteria.

* * * * *